United States Patent [19]

Eguchi et al.

[11] Patent Number: 5,082,559

[45] Date of Patent: Jan. 21, 1992

[54] GLASS CHROMATOGRAPHY CAPILLARY WITH RELATIVELY THICK COATING

[75] Inventors: Shuji Eguchi, Hitachi city, Japan; Johan G. Kloosterboer, Eindhoven, Netherlands; Dirk J. Broer, Wilmington, Del.

[73] Assignee: U.S. Philips Corporation, New York, N.Y.

[21] Appl. No.: 554,760

[22] Filed: Jul. 18, 1990

[30] Foreign Application Priority Data

Aug. 25, 1989 [NL] Netherlands ............. 8902151

[51] Int. Cl.$^5$ ............................... B01D 15/08
[52] U.S. Cl. ................. 210/198.2; 55/386; 210/198.3
[58] Field of Search ........... 210/635, 656, 198.3, 210/198.2; 55/67, 386

[56] References Cited

U.S. PATENT DOCUMENTS

| | | | |
|---|---|---|---|
| 3,663,263 | 5/1972 | Bodre | 210/198.2 |
| 3,808,125 | 4/1974 | Good | 210/198.2 |
| 3,822,530 | 4/1974 | Fuller | 55/386 |
| 4,045,353 | 8/1977 | Kosaka | 210/198.2 |
| 4,207,188 | 6/1980 | Tsuda | 210/198.2 |
| 4,242,227 | 12/1980 | Nestrick | 210/198.2 |
| 4,293,415 | 10/1981 | Bente | 210/198.2 |
| 4,483,773 | 11/1984 | Yang | 210/198.2 |
| 4,509,964 | 4/1985 | Hubball | 55/386 |
| 4,757,023 | 7/1988 | Trestianu | 55/386 |
| 4,966,785 | 10/1990 | Springston | 55/386 |

OTHER PUBLICATIONS

Van Beckel, The Application of Immobilized Liquids for Open Tubular Liquid Chromatography, Chromatographia vol. 24, 1987, pp. 739–744.

*Primary Examiner*—Ernest G. Therkorn
*Attorney, Agent, or Firm*—Norman N. Spain

[57] ABSTRACT

Glass capillaries having an internal diameter of a few micrometers are internally provided with a relatively thick polymer film by in-situ polymerization of suitable monomers and/or oligomers in a solvent. The said polymer film is suitable as a stationary phase for liquid chromatography.

2 Claims, 3 Drawing Sheets

GLASS CHROMATOGRAPHY CAPILLARY WITH RELATIVELY THICK COATING

BACKGROUND OF THE INVENTION

The invention relates to a method of manufacturing a separation column which comprises a glass capillary which is coated with a polymer film on the inside.

The invention further relates to a separation column comprising a glass capillary having an internal diameter of maximally 10 $\mu$m and, which is coated with a polymer film on the inside.

Such separation columns are used in liquid chromatography and in separation techniques which are based on the movement of particles in an electric field, such as capillary zone electrophoresis and electroendosmotic chromatography.

Liquid chromatography is a known method of separating, detecting and analysing mixtures of chemical compounds and is particularly suitable for the analysis of non-volatile or thermally unstable solid or liquid compounds such as many organic chemical compounds. The sample to be analysed is dissolved in a suitable solvent, the so-called mobile phase, and pressed through a column with the same or another suitable solvent at an increased pressure. Columns which are often used are the so-called packed columns in which a suitable absorbent in the form of porous grains is used as the stationary phase. Customarily, the grains have been subjected to a surface treatment and the thin surface layer formed serves as the stationary phase. By using a capillary, which is coated on the inside with a suitable stationary phase, instead of a packed column it is possible, in principle, to improve the separatory power of the column as well as the rate of separation. Such capillary columns are termed in literature OTLC-(Open tubular liquid chromatography) columns. It can be derived theoretically that a capillary column is superior to a packed column when the internal diameter of the capillary is 5-10 $\mu$m and the thickness of the stationary phase on the inside of the capillary is 0.3-1 $\mu$m. Owing to the difference in affinity for the stationary phase, the chemical compounds in the sample to be analysed exhibit different retention times in the chromatographic column. In this manner, the sample is separated into the individual compounds present. Detection and quantitative and/or qualitative determination of the compounds takes place at the end of the column.

A method of the type mentioned in the opening paragraph is described in an article by O. van Berkel et al. in Chromatographia 24 739-744 (1987), the contents of which are hereby incorporated by reference. In the method described in this article, a solution of a dimethylsiloxane polymer and a thermal initiator in pentane is pressed into the column. The pentane is evaporated at a reduced pressure after which crosslinking of the polymer film formed takes place at an increased temperature.

A disadvantage of the known method is the small layer thickness of the resultant polymer film in capillaries having a small internal diameter. A layer thickness of 0.045 $\mu$m is disclosed at an internal capillary diameter of 5 $\mu$m. In this case, a criterion is the phase ratio $\beta$, which is equal to $$\frac{V_s}{V_m} = \frac{(d+r)^2 - r^2}{r^2}$$

In this formula, $V_s$ is the volume of the stationary phase; $V_m$ is the volume of the mobile phase; d is the thickness of the polymer film (=stationary phase) and r is the radius of the column after the polymer film is applied. In the example given, $\beta=0.037$. The thickness of the thickest polymer film mentioned is 0.70 $\mu$m at a capillary diameter of 25.1 $\mu$m, which corresponds to a value of $\beta$ of 0.122. In general, thicker polymer layers can be obtained by increasing the concentration of the polymer in the pentane solution. However, this leads to solutions having a high viscosity so that the capillary can hardly be filled with the polymer solution. The known method is unsuitable for internally coating thin capillaries with a relatively thick polymer film. The possibility of manufacturing thick polymer films is of essential importance to the usability of the column. The maximum load (capacity) of the column increases as the thickness increases, which results in a better detection of the components.

SUMMARY OF THE INVENTION

One of the objects of the invention is to provide a method of manufacturing an OTLC column having a high phase ratio $\beta$ and, hence, a high sample capacity.

According to the invention, this object is achieved by a method as described in the opening paragraph, characterized in that the inside of the capillary is silylated after which the capillary is filled with a solution of a photo and/or thermal initiator and acrylate monomers and/or oligomers in a solvent, after which the monomers and/or oligomers are polymerized in situ by means of UV or visible light or by heating, after which the solvent is evaporated while forming the polymer film and next the polymer film is thermally postcured.

DETAILED DESCRIPTION OF THE INVENTION

Figure 1:
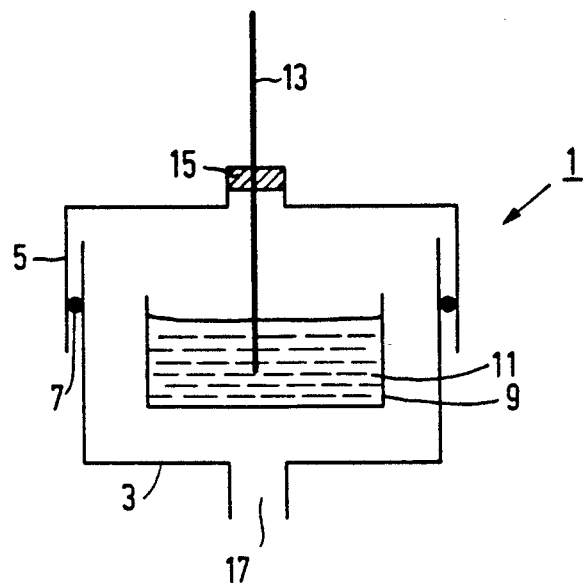
FIG. 1 is a diagrammatic cross-sectional view of a reservoir suitable for filing a capillary with a liquid.

Monomer and/or oligomer solutions have a lower viscosity than polymer solutions, thus facilitating the filling of thin capillaries. By virtue of the large choice of acrylate monomers and/or oligomers the properties of the capillary column such as the polarity of the polymer layer can be influenced.

Suitable acrylate monomers are, for example, tetraethylene glycol diacrylate (TEGDA) and 1,6-hexane diol diacrylate (HDDA). Unlike monoacrylates which in general only form linear polymer chains, diacrylates can form networks by polymerization. Tri or tetra acrylates can also be used. Examples are trimethylolpropane tri(meth)acrylate and pentaerythritol tetracrylate. Customary initiators such as $\alpha,\alpha$-dimethoxy-$\alpha$-phenylacetophenone can be used as the photoinitiator. A well known thermal initiator that may be used is azo bis isobutyronitril (AIBN). Silylation of the inside of the capillary is a surface modification of the glass surface, in which process a monolayer of a silicon-containing primer is chemically bonded to the glass surface. The primer also bonds to the polyacrylate to be formed so that this polymer is rendered immobile. Suitable silylation agents are, for example, 3-(methacryloxy)propyl-trimethoxysilane ($\gamma$-MPS) and 3-(acryloxy)propyl-trimethoxysilane ($\gamma$-APS). In addition to alkoxy silanes several other silanes containing groups that may react with —SiOH groups on the glass surface such as chloro silanes may be used. Examples are 3-methacryloxypropyltrichlorosilane and 3-acryloxypropylmethyldichlorosilane.

Also aminosilanes may be used, such as 4-aminobutyl-triethoxysilane.

These silanes are dissolved in, for example, toluene after which the solution is pumped through the capillary at an increased temperature. After washing with toluene and drying the capillary is filled with the solution of the acrylate monomers and/or oligomers and the photoinitiator. For example, chloroform is used as the solvent.

After exposure to UV light having a wavelength of approximately 350 nm, polymerization takes place. In this process the wavelength and the absorption maximum of the photoinitiator are attuned. Dependent upon the length of the capillaries two methods of exposure are used. In the case of capillaries having a length up to 60 cm a suitable gas-discharge lamp having a length of 60 cm is used. In the case of capillaries having a length exceeding 60 cm, the capillary is passed along a gas-discharge lamp having a length of, for example, 120 cm at a constant velocity. In this manner, a swollen network throughout the capillary of polyacrylate is formed, the spaces between the molecules being filled with solvent. The solvent is evaporated by connecting the capillary to a vacuum pump on one side. The polymer network collapses and a polymer film is formed on the inside of the capillary. In the case of unsilylated capillaries a polymer thread would be formed under the same conditions. By virtue of the chemical bond between the glass wall and the polymer via an adhesive silane, a uniform film is formed. Subsequently, a further curing of the polymer film takes place at an increased temperature, for example 120° C. The latter treatment brings about additional crosslinking of the polymer, thus precluding a too high degree of swelling during the use of the column in liquid chromatographic analysis.

The material of the capillary is glass, preferably quartz glass because it has better chemical properties. The capillary is protected on the outside by an organic coating layer such as polyacrylate or polyimide. Capillaries of quartz glass are drawn at a temperature of approximately 2000° C., which results in a low degree of occupation of silanol groups (—Si—OH) at the quartz surface. At least a part of the siloxane groups has to be converted into silanol groups because in the silylation reaction the silane reacts with a silanol group but not with a siloxane group (—Si—O—Si—). For this purpose, first a solution of KOH is pumped through the quartz capillary, and subsequently a HCl solution. In this operation, the siloxane groups are converted into silanol groups and the excess of lye is removed. Subsequently, the silylation reaction is carried out.

Using the method according to the invention, capillaries having an internal diameter of 9 $\mu$m can be provided with a polymer film with a thickness of 0.3 $\mu$m ($\beta$-value=0.148) on the inside. Capillaries having a larger diameter can also be coated with a thick polymer film on the inside. Using the method according to the invention, for example, a capillary having an internal diameter of 65 $\mu$m is coated with a polymer film having a thickness of 5 $\mu$m ($\beta$-value=0.397). Despite the high value of $\beta$, columns manufactured by means of the method according to the invention exhibit a low value of the theoretical plate height H (HETP=Height Equivalent to a Theoretical Plate) and, by virtue of the high value of $\beta$, a satisfactory signal/noise ratio in the chromatogram being obtained. The H-value is a measure of the separatory power of the column and depends, among other things, on the linear flow rate of the mobile phase.

Figure 6:
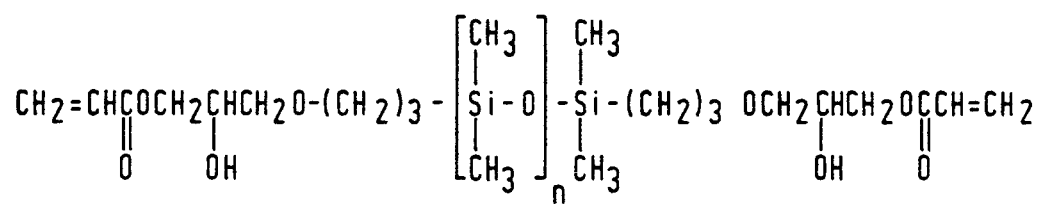
FIG. 6 shows the formula of siloxane acrylate (Tegomer V-Si 2150) in which n$\approx$9.

An embodiment of the method according to the invention is characterized in that a siloxane acrylate oligomer is used as the acrylate. Such an acrylate is marketed by Th. Goldschmidt A. G. under type number RC 710. This liquid has a low viscosity of 200 mPa.s. at room temperature. The advantage of siloxane acrylate relative to other acrylates such as TEGDA and HDDA is the lower surface tension. This results in a better moistening of the silylated glass surface, thus promoting a uniform layer thickness. Moreover, polymerized siloxane acrylate is more resistant to swelling when polar solvents such as water and methanol are used, as is the case in "reversed-phase" liquid chromatography. In comparison with other polyacrylates, polymerized siloxane has the additional advantage of a high diffusion coefficient for dissolved compounds due to the flexible polymer chain. The use of polymerized TEGDA or HDDA could cause the capillary to become clogged as a result of a too high degree of swelling. In addition to RC 710 the similar compounds RC 705 and RC 720 and Tegomer V-Si 2150 or mixtures thereof may be used. The compounds differ in the length of their siloxane chain. All these siloxane acrylates have at least two (meth)acrylate groups per molecule. Other but rather similar compounds are sold by Petrarch Systems, Bristol, Pa., with type numbers PS 583, PS 802, PS 851 and PS 074.4. The formula of Tegomer V-Si 2150 is shown in FIG. 6, in which n$\approx$9.

Another embodiment of the method according to the invention is characterized in that the acrylate monomers and/or oligomers are mixed with monoacrylates. Monoacrylates are acrylates having one acrylate group per molecule and do not form networks on polymerization but form linear polymer molecules. When acrylate monomers having two or more acrylate groups per molecule, such as TEGDA, HDDA and siloxane acrylate, are mixed with monoacrylates a reduced cross-link density is obtained after polymerization. A smaller network density enhances the evaporation of the solvent after the polymerization reaction as well as the diffusion of the mobile phase and the components dissolved therein. Another method of controlling the network density consists in varying the exposure dose. The latter method has yielded less favourable results in practice because polymerization continues for a while in the dark. Suitable monoacrylates are, for example, lauryl acrylate (LA), ethoxy-ethyl acrylate (EEA), 2-ethylhexyl acrylate and cyclohexylmethacrylate. LA and TEGDA are mixed, in a ratio of, for example, 2:1 (W/W) to prepare a 20 wt. % solution in chloroform. In particular a monomer mixture of LA and siloxane acrylate yields a very good film uniformity after polymerization, the film obtained being resistant to methanol and other polar solvents, which prevents the capillary from becoming clogged during operation as a result of swelling.

In chromatography various modifications of silicone gums are commonly used in order to vary the polarity and solubility of the stationary phase. The siloxanes used may contain phenyl, cyano or other groups. Such gums may be dissolved in the starting solution and upon polymerization they will become physically and or chemically attached to the network formed by the (meth)acrylate siloxane oligomer and, for example, LA. Some examples of modified gums are polydimethylsiloxane-(5-6%)-(diphenyl)-(0.1-0.3%)-methylvinylsiloxane copolymer and polycyanopropylmethylsiloxane.

A further embodiment of the method according to the invention is characterized in that tetrahydrofurane (THF) is used as the solvent. The use of THF as the solvent for acrylate monomers and/or oligomers has the advantage that higher monomer and/or oligomer concentrations can be used (for example 30% by weight) than in the case of solvents such as chloroform. Higher monomer and/or oligomer concentrations lead to a thicker polymer film.

A further object of the invention is to provide, inter alia a separation column which comprises a glass capillary having an internal diameter of maximally 10 $\mu$m which is coated with a polymer film on the inside, which column has a better combination of separatory power and capacity than the column according to the state of the art. The signal/noise ratio is better than that of known OTLC columns.

According to the invention, this object is achieved by a liquid chromatographic column which is further characterized in that the ratio between the volume of the polymer film and the internal volume of the capillary after the polymer film has been applied is larger than 0.14. As has been stated above, in literature this ratio is termed the phase ratio $\beta$. In the above-identified article by O. van Berkel et al. a maximum film thickness of 0.70 $\mu$m is disclosed at an internal capillary diameter of 25.1 $\mu$m, which corresponds to a $\beta$-value of 0.122. The columns mentioned which have an internal diameter of 25 $\mu$m and film thicknesses of 0.25 $\mu$m and 0.38 $\mu$m, respectively, have a plate height H of 150 and 350 $\mu$m, respectively, for specific polycyclic aromatics at a linear velocity v of the mobile phase of 5.7 mm/s. A column according to the invention has, for example, an internal capillary diameter of 9 $\mu$m and a polymer film thickness of 0.3 $\mu$m, which corresponds to a $\beta$-value of 0.148. With such a column and under the same conditions H-values are attained ranging between 20 and 40 $\mu$m, which is an improvement of the separatory power. The important advantage obtained is that at the same or even an improved separatory power the signal/noise ratio in the chromatogram improves substantially by virtue of the presence of the relatively thick polymer film, thus enabling a relatively high loading of the column. This is very favourable for the detection of small quantities of a chemical component in a sample.

It should be noted that the U.S. Pat. No. 3,808,125 discloses a process for internally coating a capillary with a polymeric film. In that process the capillary is filled with a solution comprising a solvent and monomers. Subsequently the solvent is evaporated leaving a thin monomer film on the inside of the capillary, after which the monomers are polymerized. In order to obtain thick films, as required in liquid chromatography, this process has to be repeated as many times as necessary. In the process according to the present invention the monomers and/or oligomers are first polymerized throughout the capillary leading to a swollen network of polyacrylate, after which the solvent is evaporated. The collapsing polymer network yields a thick polymer film on the inside of the capillary.

The invention will be explained in greater detail by means of the following exemplary embodiments and with reference to the accompanying drawings.

EXEMPLARY EMBODIMENT 1

Figure 2:
FIG. 2 shows diagrammatically the formation of silanol groups on the quartz glass surface after treatment of the surface with KOH and HCl.

A quartz capillary having a length of 1 m and an internal diameter of 65 $\mu$m is etched with a KOH solution on the inside. For this purpose, a reservoir is used as described in the above mentioned article by O. van Berkel et al. In FIG. 1 the reservoir is denoted by reference numeral 1. This reservoir is composed of a steel vessel 3 having a lid 5, a seal 7 being provided between the vessel and the lid. A glass beaker 9 containing a 1M KOH solution 11 is provided in the vessel. A capillary 13 to be filled is passed through the lid 5 via a stopper 15, the end portion of the capillary being in the solution 11. Helium is pressed through an aperture 17 in the vessel 3 at a pressure of 5 bar, so that the solution 11 is pressed through the capillary. The KOH solution remains in the capillary for 2 hours after which the capillary is, washed with, in succession, water and 0.03M HCl and finally again with water until the water coming out of the capillary is neutral. The same reservoir as shown in FIG. 1 is used for the washing treatments, the solution 11 being replaced by water, HCl and water, respectively. As a result of this treatment, the siloxane groups of the quartz surface are converted into silanol groups, as schematically shown in FIG. 2. Subsequently, the capillary is dried at 125° C., using a helium flow, for at least 4 hours.

Figure 3:
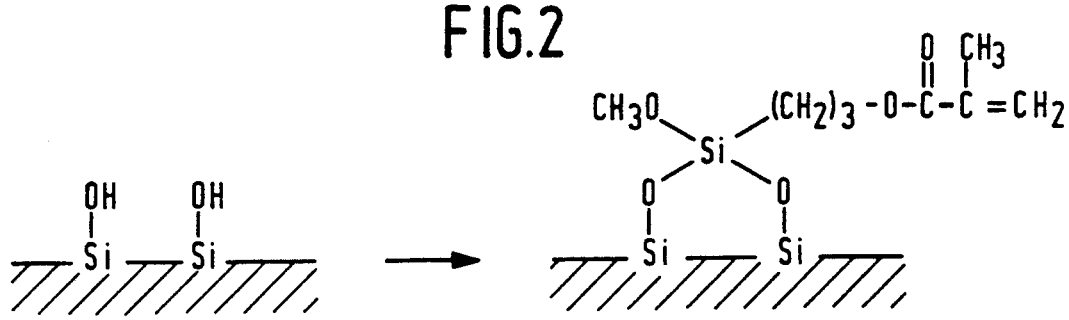
FIG. 3 shows diagrammatically a silyation reaction on the quartz glass surface after the formation of the silanol groups.

The silylation process is carried out by means of a 1 vol. % solution of 3-(methacryloxy)propyltrimethoxysilane ($\gamma$-MPS, Ventron) in toluene. This solution is pressed into the capillary by means of the reservoir of FIG. 1, solution 11 representing the silane solution. Silylation takes place at 125° C. for 1 hour, for which purpose the capillary is introduced into a furnace. Subsequently, the capillary is washed with toluene and dried at room temperature using a helium flow for at least 3 hours. As a result of this reaction, the capillary surface is provided with a chemically bonded monolayer of methacrylate groups, as diagrammatically shown in FIG. 3.

A solution which is composed of siloxane acrylate (RC710, Th. Goldschmidt A. G.) and lauryl acrylate (Polysciences Inc.) in a mass ratio of 1:1 and tetrahydrofurane (THF) as the solvent is prepared as the monomer/oligomer solution. The concentration of acrylate monomers is 30% by weight. 2% by weight of $\alpha,\alpha$-dimethoxy-$\alpha$-phenyl-acetophenone (Irgacure 651, Ciba Geigy) is added to this solution as the photoinitiator.

The capillary pretreated as described above is filled with this monomer solution by immersing one end portion of the capillary in the monomer solution and connecting the other end portion to a vacuum pump (150 mbar). The filled capillary is subsequently subjected to UV radiation having a wavelength of approximately 350 nm and a radiation intensity of 0.35 mW/cm². For this purpose, the capillary is led along a UV lamp (Philips, TLD 36W/08, length 120 cm) at a rate of 2 mm/s. Polymerization occurs as a result of when a network of polyacrylate is formed in the capillary which is chemically bonded to the quartz glass surface of the capillary via the silane. The solvent THF is present within the network. Subsequently, one end portion of the capillary is connected to a vacuum pump (pressure 150–250 mbar) for at least 15 hours, so that the solvent evaporates and the polymer network collapses, while forming a polymer film on the inside of the capillary. Finally, the polymer film is postcured thermally at 120° C. for 12 hours. The latter treatment precludes the film from swelling too much during operation of the column in a chromatographic analysis. The thickness of the polymer film is measured by picking up a SEM-(scanning electron microscope) image of a perpendicular cross-section of the capillary and is 5 $\mu$m, which corresponds to a $\beta$-value of 0.397.

EXEMPLARY EMBODIMENT 2

Exemplary embodiment 1 is repeated using a quartz capillary having an internal diameter of 9 $\mu$m and a length of 1 m. The thickness of the polymer film obtained is 0.3 $\mu$m, which corresponds to a $\beta$-value of 0.148.

EXEMPLARY EMBODIMENT 3

The chromatographic properties of a 9 $\mu$m capillary having a length of 75 cm, which is obtained in accordance with exemplary embodiment 2, are measured of a OTLC arrangement as described in the above-mentioned article by O. van Berkel et al. This arrangement is composed of a steel vessel having a content of 400 ml to which a pressure is applied by means of helium. This vessel contains the eluent or mobile phase. The vessel is connected to the capillary through a filter, a 0.5 $\mu$l injection valve and a splitter. The protective polyacrylate layer of the capillary is burned off at the end portion over a distance of approximately 2 cm. A HeCd laser (wavelength 325 nm) in combination with a fluorimeter as the photodetector are used for on-column fluorescence detection.

Figure 4:
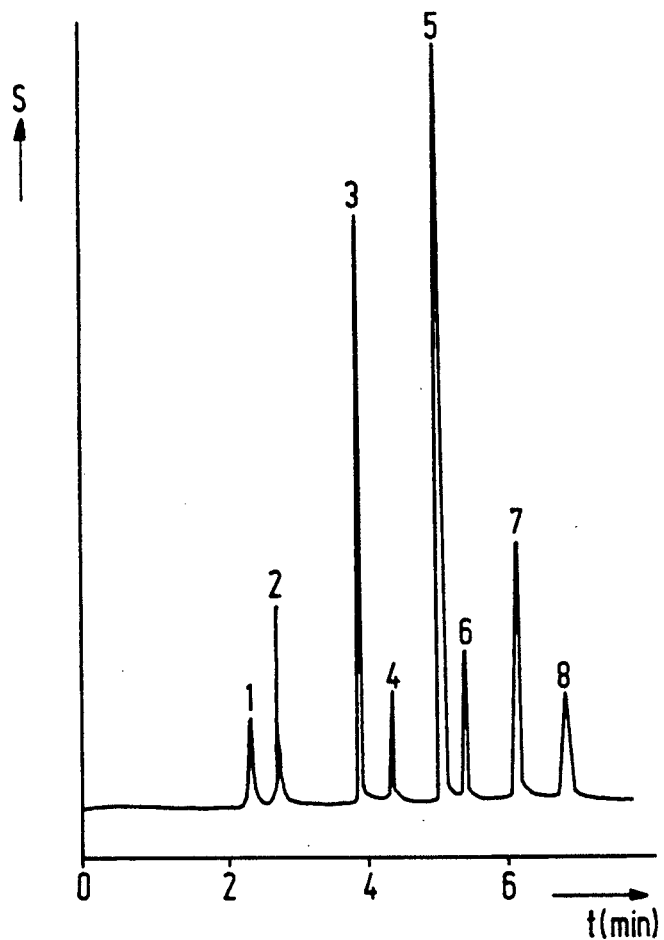
FIG. 4 shows a chromatogram of anthracene derivatives derived by use of a column according to the invention.

The chromatographic properties of the column are tested by means of a mixture of anthracene derivatives in methanol, namely anthracene, 9-cyanoanthracene, 9-(hydroxymethyl)anthracene, fluoroanthene, 9-phenylanthracene, 1,2-benzanthracene and 9,10-diphenylanthracene. Methanol is used as the mobile phase, the linear velocity through the column being 5.6 mm/s. By means of the injection valve and the splitter, 15 picoliter of the sample is pressed into the column. FIG. 4 shows the chromatogram obtained, the retention time t in minutes being plotted along the horizontal axis and the detected signal in arbitrary units being plotted along the vertical axis. In the chromotogram, the digits at the peaks represent, besides the reference substance fluorescein, the following anthracene derivatives:

1 = fluorescein
2 = 9-(hydroxymethyl)anthracene
3 = 9-cyanoanthracene
4 = anthracene
5 = fluoroanthene
6 = 9-phenylanthracene
7 = 1,2-benzanthracene
8 = 9,10-diphenylanthracene.

Figure 5:
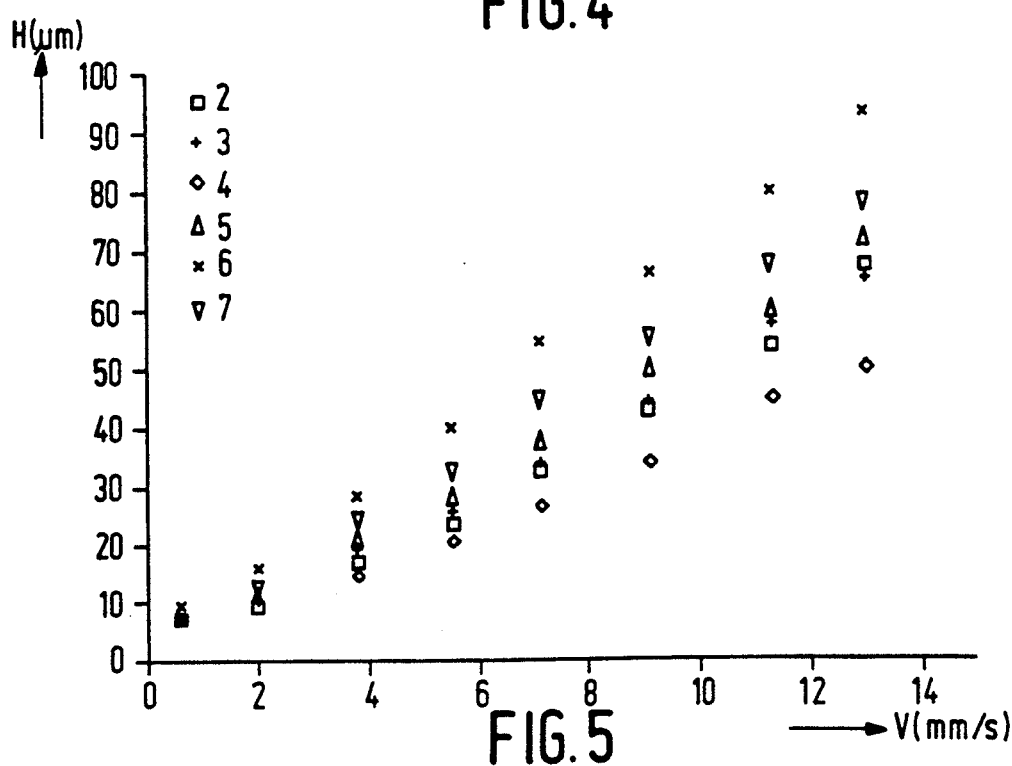
FIG. 5 is a graph of METP (height equivalent to a theoretical plate) of a column of the invention plotted against the linear velocity of the mobile phase.

The signal obtained hardly contains any noise (high signal/noise ratio), thus enabling also small concentrations to be detected. The signal obtained using a column as described in the said article by O. van Berkel et al., which column has a polymer thickness of 0.028 $\mu$m, contains a lot of noise (see FIG. 10 in the said article). The signal/noise ratio could be improved by higher concentrations, but this would lead to the column being overloaded which results in an undesirable peak broadening. The performance of the column according to the invention is shown in FIG. 5. The plate height H in $\mu$m is plotted for the various anthracene derivatives against the linear velocity v in mm/s of the mobile phase. The plate heights are approximately a factor of 10 lower than those shown in the article by O. van Berkel et al., which is an indication of a better separatory power. The numbers in FIG. 5 correspond to the same anthracene derivatives as in FIG. 4.

We claim:

1. A separation column comprising a glass capillary having an internal diameter of maximally 10 $\mu$m which is coated with a polymer film on the inside, wherein in the ratio between the volume of the polymer film and the internal volume of the capillary after the polymer film has been applied is larger than 0.14.

2. A separation column comprising a glass capillary having an internal diameter of maximally 10 $\mu$m coated on its internal surface with a polymer film provided thereon by the method comprising silylating the inside of the capillary then filling the capillary with a solution of a photo initiator and/or thermal initiator and acrylate monomers and/or acrylate oligomers in a solvent, polymerizing the monomers in situ by means of UV or visible light or by heating, evaporating the solvent while forming the resultant polymer film and thermally postcuring said polymer film and wherein the ratio between the volume of said polymer film and the internal volume of the capillary after application of the polymer film is larger than 0.14.

* * * * *